United States Patent [19]

Ponsford et al.

[11] Patent Number: 5,126,335
[45] Date of Patent: Jun. 30, 1992

[54] PENICILLINS CONTAINING AN ACRYLAMIDE SIDE CHAIN

[75] Inventors: Roger J. Ponsford; Andrew V. Stachulski, both of Betchworth, England

[73] Assignee: Beecham Group p.l.c., England

[21] Appl. No.: 496,777

[22] Filed: Mar. 21, 1990

[30] Foreign Application Priority Data

Mar. 22, 1989 [GB] United Kingdom ............... 8906592

[51] Int. Cl.[5] ...................... A61K 31/43; C07D 499/70
[52] U.S. Cl. .................................... 514/195; 514/196; 540/316; 540/328
[58] Field of Search ............... 540/316, 328; 514/195, 514/196

[56] References Cited

U.S. PATENT DOCUMENTS 4,416,880  11/1983  Boberg et al. ................. 540/328 X Primary Examiner—Jose G. Dees
Assistant Examiner—Vera C. Clarke
Attorney, Agent, or Firm—Rosenman & Colin

[57] ABSTRACT

Compounds of formula (I) and pharmaceutically acceptable salts and in-vivo hydrolysable esters thereof:

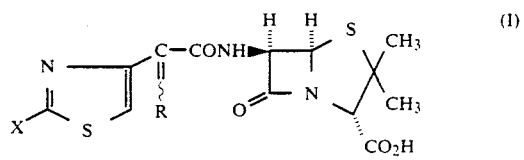

wherein X is hydrogen or a group $NHR^1$, wherein $R^1$ is hydrogen or an amino protecting group, and R is an optionally substituted 5-membered or 6-membered saturated heterocyclic group containing 1 or 2 heteroatoms selected from oxygen, sulphur or nitrogen, are useful in the treatment of bacterial infections in humans and animals.

13 Claims, No Drawings

PENICILLINS CONTAINING AN ACRYLAMIDE SIDE CHAIN

This invention relates to novel β-lactam containing compounds, their preparation and their use, and in particular to a novel class of penicillins. These compounds have antibacterial properties, and therefore are of use in the treatment of bacterial infections in humans and animals caused by a wide range of organisms.

U.S. Pat. No. 3,622,569, U.S. Pat. No. 4,416,880 and EP-A-0161617 disclose β-lactam antibiotics containing a substituted acrylamido side chain.

We have now found a particular class of penicillin antibiotics containing a substituted acrylamido side chain that possesses high antibacterial activity and a high level of stability to bacterial β lactamases.

The present invention accordingly provides a compound of formula (I) or a pharmaceutically acceptable salt or in-vivo hydrolysable ester thereof:

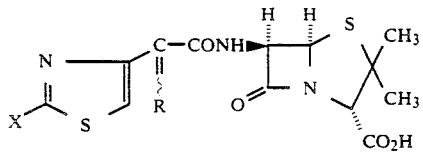

wherein X is hydrogen or a group $NHR^1$, wherein $R^1$ is hydrogen or an amino protecting group, and R is an optionally substituted 5-membered or 6-membered saturated heterocyclic group containing 1 or 2 heteroatoms selected from oxygen, sulphur or nitrogen.

Compounds of the invention may exist in two or more tautomeric forms, e.g. those having the partial structures below:

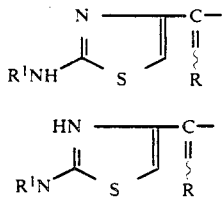

It should be understood that all tautomeric forms of the compound of formula (I) are included within the scope of the invention.

The group R may be substituted with one or more groups selected from $C_{1-6}$ alkyl, $C_{1-6}$ alkanoyl, $C_{1-6}$ alkoxy, halogen and $C_{3-7}$ cycloalkyl.

A preferred value of R within the present invention is tetrahydropyranyl.

Suitable amino protecting groups $R^1$ are those well known in the art which may be removed under conventional conditions without disruption of the remainder of the molecule.

Examples of amino protecting groups $R^1$ include $C_{1-6}$ alkanoyl; benzoyl or benzyl optionally substituted in the phenyl ring by one or two substituents selected from $C_{1-4}$ alkyl, $C_{1-4}$ alkoxy, trifluoromethyl, halogen, or nitro; $C_{1-4}$ alkoxycarbonyl; benzyloxycarbonyl or trityl substituted as for benzyl above; allyloxycarbonyl, trichloroethoxycarbonyl or chloroacetyl. Examples of suitable pharmaceutically acceptable in vivo hydrolysable ester groups include those which break down readily in the human body to leave the parent acid or its salt. Suitable ester groups of this type include those of part formula (i), (ii), (iii) and (iv):

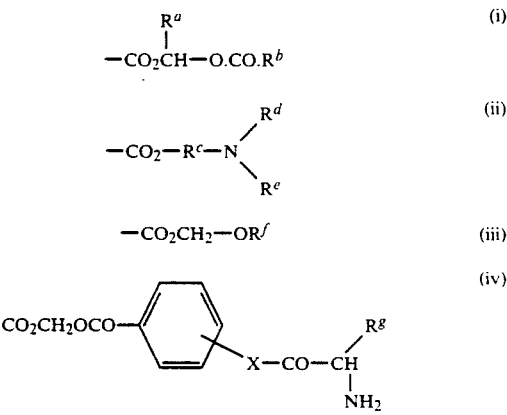

wherein $R^a$ is hydrogen, $C_{1-6}$ alkyl, $C_{3-7}$ cycloalkyl, methyl, or phenyl, $R^b$ is $C_{1-6}$ alkyl, $C_{1-6}$ alkoxy, phenyl, benzyl, $C_{3-7}$ cycloalkyl, $C_{1-6}$ alkyl $C_{3-7}$ cycloalkyl, 1-amino $C_{1-6}$ alkyl, or 1-($C_{1-6}$ alkyl)amino $C_{1-6}$ alkyl; or $R^a$ and $R^b$ together form a 1,2-phenylene group optionally substituted by one or two methoxy groups; $R^c$ represents $C_{1-6}$ alkylene optionally substituted with a methyl or ethyl group and $R^d$ and $R^e$ independently represent $C_{1-6}$ alkyl; $R^f$ represents $C_{1-6}$ alkyl; $R^g$ represents hydrogen or phenyl optionally substituted by up to three groups selected from halogen, $C_{1-6}$ alkyl, or $C_{1-6}$ alkoxy; and X is (preferably o) oxygen or (preferably o or p)NH.

Examples of suitable in vivo hydrolysable ester groups include, for example, acyloxyalkyl groups such as acetoxymethyl, pivaloyloxymethyl, α-acetoxyethyl, α-pivaloyloxyethyl, 1-(cyclohexylcarbonyloxy)prop-1-yl, and (1-aminoethyl)carbonyloxymethyl; alkoxycarbonyloxyalkyl groups, such as ethoxycarbonyloxymethyl and α-ethoxycarbonyloxyethyl; dialkylaminoalkyl especially di-loweralkylamino alkyl groups such as dimethylaminomethyl, dimethylaminoethyl, diethylaminomethyl or diethylaminoethyl; lactone groups such as phthalidyl and dimethoxyphthalidyl; and esters linked to a second β-lactam antibiotic or to a β-lactamase inhibitor.

A further suitable pharmaceutically acceptable in vivo hydrolysable ester group is that of the formula:

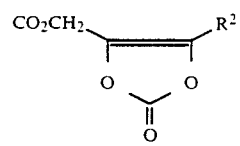

wherein $R^2$ is hydrogen, $C_{1-6}$ alkyl or phenyl.

The in-vivo hydrolysable esters of compounds of formula (I) are preferred where the antibiotic is for oral administration.

Suitable pharmaceutically acceptable salts of the carboxy group of the compound of formula (I) include metal salts, e.g. aluminium, alkali metal salts such as sodium or potassium, alkaline earth metal salts such as calcium or magnesium and ammonium or substituted ammonium salts, for example those with lower alkylamines such as triethylamine, hydroxy-lower alkylamines such as 2-hydroxyethylamine, bis-(2-hydroxyethyl)-amine or tris-(2-hydroxyethyl)amine, cycloalkylamines such as dicyclohexylamine, or with procaine, dibenzylamine, N,N-dibenzylethylenediamine, 1-ephenamine, N-ethylpiperidine, N-benzyl-β-phenethylamine, dehydroabietylamine, N,N'-bisdehydroabietylamine, ethylenediamine, or bases of the pyridine type such as pyridine, collidine or quinoline, or other amines which have been used to form salts with known penicillins and cephalosporins.

Some of the compounds of this invention may be crystallised or recrystallised from solvents such as methanol. In such cases solvates may be formed. This invention includes within its scope stoichiometric solvates including hydrates as well as compounds containing variable amounts of water that may be produced by processes such as lyophilisation.

Since the compounds of the formula (I) and their salts and in-vivo hydrolysable esters are intended for use in pharmaceutical compositions it will readily be understood that they are each provided in substantially pure form, for example at least 60% pure, more suitably at least 75% pure and preferably at least 85%, especially at least 95% pure (% are on a weight for weight basis). Impure preparations of the compounds of the formula (I) and their salts may be used for preparing the more pure forms used in the pharmaceutical compositions; these less pure preparations of the compounds of formula (I) and their salts should contain at least 1%, more suitably at least 5% and preferably from 10 to 49% of a compound of the formula (I) or salt thereof.

Compounds of the present invention may exist as either syn or anti isomers, or may exist as mixtures of syn and anti isomers containing at least 75% of one such isomer, or preferably at least 90% of one such isomer.

Herein the terms syn and anti refer to the configuration of the group R with respect to the carboxamido group, the syn-configuration (sometimes called the Z-configuration) being denoted thus:

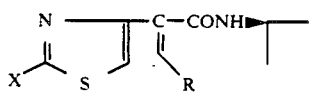

and the anti configuration (sometimes called the E-configuration) being denoted thus:

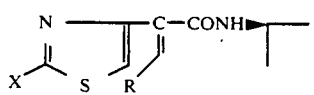

A preferred compound of the present invention is the syn-isomer of the formula (IA):

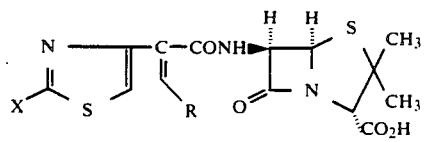

wherein R and X are as hereinbefore defined.

The compounds of formula (I) may be prepared by treating a compound of formula (II) or salt thereof:

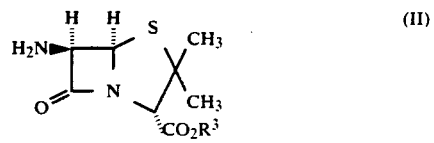

wherein the amino group is optionally substituted with a group which permits acylation to take place, and $R^3$ is hydrogen or a readily removable carboxyl blocking group; with an acylating agent derived from the acid of formula (III):

wherein Y is a group of formula:

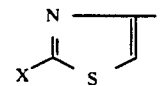

or a group which is convertable thereto, and R and X are as defined with respect to formula (I).

Any of the following reactions in any appropriate sequence may then be carried out:-
(i) removal of any amino-protecting group $R^1$;
(ii) removal of any carboxyl blocking group $R^3$;
(iii) formation of a pharmaceutically acceptable salt;
(iv) conversion of a carboxyl group into an ester function such as an in vivo hydrolysable ester.
(v) conversion of group Y to a group of formula

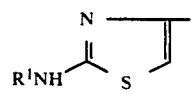

Suitable groups which permit acylation to take place and which are optionally present on the amino group of the starting material of formula (II) include N-silyl, N-stannyl and N-phosphorus groups, for example trialkylsilyl groups such as trimethylsilyl, trialkyltin groups such as tri-n-butyltin, groups of formula -PR$^a$R$^b$ wherein R$^a$ is an alkyl, haloalkyl, aryl, aralkyl, alkoxy, haloalkoxy, aryloxy, aralkoxy or dialkylamino group, R$^b$ is the same as R$^a$ or is halogen or R$^a$ and R$^b$ together form a ring; suitable such phosphorus groups being —P(OC$_2$H$_5$)$_2$, —P(C$_2$H$_5$)$_2$,

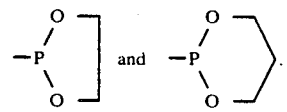

Suitable carboxyl-blocking derivatives for the group CO$_2$R$^3$ in formula (II) include salts and ester derivatives of the carboxylic acid. The derivative is preferably one which may readily be cleaved at a later stage of the reaction. Suitable salts include metal salts, such as those with sodium, potassium and lithium, a preferred salt is sodium.

Suitable ester-forming carboxyl-blocking groups are those which may be removed under conventional conditions. Such groups for $R^3$ include benzyl, p-methoxybenzyl, 2,4,6-trimethylbenzyl, 3,5-di-t-butyl-4-hydroxybenzyl, benzoylmethyl, p-nitrobenzyl, 4-pyridylmethyl, 2,2,2-trichloroethyl, 2,2,2-tribromoethyl, t-butyl, t-amyl, diphenylmethyl (benzhydryl), triphenylmethyl, adamantyl,2-benzyloxyphenyl, 4-methylthiophenyl, tetrahydrofuran-2-yl, tetrahydropyran-2-yl, pentachlorophenyl, p-toluenesulphonylethyl, methoxymethyl, a silyl, stannyl or phosphorus-containing group, such as described above, an oximeradical of formula $-N=CHR^4$ where $R^4$ is aryl or heterocyclic, or an in vivo hydrolysable ester radical such as defined above.

The carboxyl group may be regenerated from any of the above esters by usual methods appropriate to the particular $R^3$ group, for example, acid—and base—catalysed hydrolysis, or by enzymically—catalysed hydrolysis, or by hydrogenation under conditions wherein other parts of the molecule are unaffected.

A reactive N-acylating derivative of the acid of formula (III) is employed in the above process. The group $R^1$ in the acid of formula (III), when present, will be chosen such that the group $NHR^1$ does not react when the carboxy group in (III) is converted into the said N-acylating derivative. Thus, in many—although not all—of the suitable N-acylating derivatives of the acid (III) detailed below, $R^1$ cannot be hydrogen.

Suitable N-acylating derivatives of the acid (III) include acid (III) halides, preferably the acid chloride or bromide. Acylation with an acid halide may be effected in the presence of an acid binding agent, for example a tertiary amine (such as triethylamine or dimethylaniline), an inorganic base (such as calcium carbonate or sodium bicarbonate), molecular sieves (such as type 4 Angstroms) or an oxirane, which binds hydrogen halide liberated in the acylation reaction. The oxirane is preferably a $(C_{1-6})$- 1,2-alkylene oxide —such as ethylene oxide or propylene oxide. The acylation reaction using an acid halide may be carried out at a temperature in the range $-50°$ C. to $+50°$ C., preferably -20° C. to +20° C., in aqueous or non-aqueous media such as aqueous acetone, aqueous tetrahydrofuran, ethyl acetate, dimethylacetamide, dimethylformamide (DMF), acetonitrile, dichloromethane, 1,2-dichloroethane, or mixtures thereof. Alternatively, the reaction may be carried out in an unstable emulsion of water-immiscible solvent, especially an aliphatic ester or ketone, such as methyl isobutyl ketone or butyl acetate.

The acid halide may be prepared by reacting the acid (III) with a halogenating (e.g. chlorinating or brominating) agent such as phosphorus pentachloride, thionyl chloride or oxalyl chloride.

Alternatively, the N-acylating derivative of the acid (III) may be a symmetrical or mixed anhydride. Suitable mixed anhydrides are alkoxyformic anhydrides, or anhydrides with, for example, carbonic acid monoesters, trimethyl acetic acid, thioacetic acid, diphenylacetic acid, benzoic acid, phosphorus acids (such as phosphoric or phosphorous acids) or aliphatic or aromatic sulphonic acids (such as methanesulphonic acid and p-toluenesulphonic acid respectively). When a symmetrical anhydride is employed, the acylation reaction may be carried out in the presence of an organic base such as 2,6-lutidine as catalyst.

When a mixed anhydride is employed the N-acylating derivative is preferably prepared in the presence of an organic base such as triethylamine and/or N,N-diisopropylethylamine in a suitable solvent such as DMF at between $-50°$ C. and room temperature. Alternatively, the N-acylating derivative may be prepared from an alkali metal salt of the acid of formula (III), such as the sodium salt, in a suitable solvent such as DMF at between $-50°$ C. and room temperature. The N-acylating derivative of the acid of formula (III) so derived may then be reacted with a compound of formula (II). The acylation reaction may conveniently be carried out at $-50°$ C. to $+50°$ C. in a suitable solvent such as water, acetonitrile or DMF at a temperature of not more than 0° C. The reaction may be carried out in the presence of a suitable base such as triethylamine or sodium hydrogen carbonate.

A further method of forming the N-acylating derivative of the acid of formula (III) is to treat the acid of formula (III) with a solution or suspension preformed by addition of a carbonyl halide, preferably oxalyl chloride, or a phosphoryl halide such as phosphorus oxychloride, to a halogenated hydrocarbon solvent, preferably dichloromethane, containing a lower acyl tertiary amide, preferably N,N-dimethylformamide. The N-acylating derivative of the acid of formula (III) so derived may then be caused to react with a compound of formula (II). The acylation reaction may conveniently be carried out at $-40°$ to $+30°$ C., if desired in the presence of an acid binding agent such as trithylamine. A catalyst such as 4-dimethylaminopyridine may optionally also be added. Other suitable acylating agents derived from the acid of formula (III) are thioesters of formula (IV)

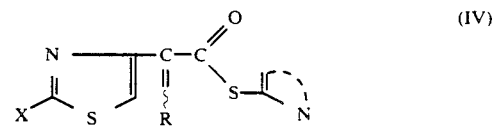

(IV)

wherein R and X are as hereinbefore defined and

represents a 5- or 6-membered heterocyclic ring. which may contain, in addition to the nitrogen atom, one or two further heteroatoms, selected from oxygen, nitrogen and sulphur and which may be substituted or fused to a benzene ring which may itself be substituted.

Particular acylating agents derived from the acid of formula (III) are the thio esters (IVa) or (IVb)

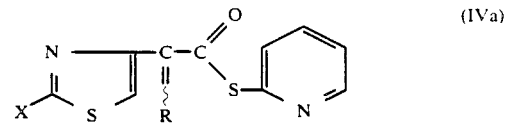

(IVa)

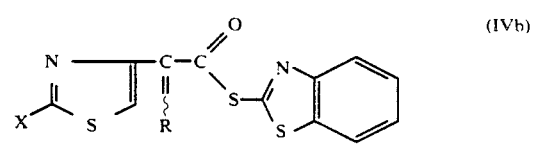

(IVb)

wherein R and X are as hereinbefore defined.

Compounds of the formula (IVa) and (IVb) may be prepared by treatment of the acid (III) with 2,2'-dipyridyldisulphide or 2,2'-dibenzothiazolyldisulphide respectively, in the presence of triphenylphosphine, analogously to the routes described in EP-A-0037380. Conveniently, in compounds of the formula (IVa) and (IVb), $R^1$ may be hydrogen.

Other suitable N-acylating derivatives of acid (III) include the ac-d azide; the activated esters derived from cyanomethanol; p-nitrophenol; 2,4-dinitrophenol; thiophenol; halophenols, including pentachlorophenol; monomethoxyphenol; N-hydroxy succinimide; N-hydroxybenzotriazole or 8-hydroxyquinoline; or include amides such as N-acylsaccharins, N-acylthiazolidin-2-thione or N-acylphthalimides; or an alkylidene iminoester prepared by reaction of the acid (III) with an oxime.

Other reactive N-acylating derivatives of the acid (III) include the reactive intermediates formed by reaction in situ with a condensing agent such as a carbodiimide, for example, N,N'-diethyl-, dipropyl- or diisopropylcarbodiimide, N,N'-di-cyclohexylcarbodiimide, or N-ethyl-N'[3-(dimethylamino)propyl]carbodiimide; a suitable carbonyl compound, for example, N,N'-carbonyldiimidazole or N,N'-carbonylditriazole; an isoxazolinium salt, for example, N-ethyl-5-phenylisoxolinium-3-sulphonate or N-7-butyl-5-methylisoxazolinium perchlorate; or an N-alkoxycarbonyl 2-alkoxy-1,2-dihydroquinoline, such as N-ethoxycarbonyl 2-ethoxy-1,2-dihydroquinoline. Other condensing agents include Lewis acids (for example $BBr_3 - C_6H_6$); or a phosphoric acid condensing agent such as diethylphosphorylcyanide. The condensation reaction is preferably carried out in an organic reaction medium, for example, methylene chloride, dimethylformamide, acetonitrile, alcohol, benzene, dioxan or tetrahydrofuran.

Compounds of formula (III) may be prepared by routes analogous to those disclosed in U.S. Pat. No. 3,622,569, U.S. Pat. No. 4,416,880, U.S. Pat. No. 4,500,716 and EP-A-0 161 617.

In particular compounds of formula (III) may be prepared by condensation of an aldehyde of formula RCHO with an ester, such as the methyl ester, of the acid $YCH_2COOH$ wherein R and Y are as hereinbefore defined.

Any of the following reactions in any appropriate sequence may then be carried out:

(i) conversion of Y to a group of formula:

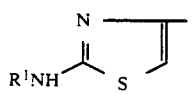

(ii) separation of E and Z isomers,
(iii) deamination of a group of formula:

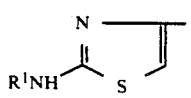

(iv) removal of a protecting group $R^1$ when present, and (v) hydrolysis of an ester of the acid of formula (III).

The condensation reaction is typically carried out at low temperatures, e.g. about $-10°$ C., in the presence of a base such as piperidine, or by reflux with acetic acid-piperidine catalysis in benzene or toluene and azeotropic removal of water.

Separation of E and Z isomers can be effected by chromatography, for example by silica gel chromatography in an ethyl acetate-hexane solvent system.

Processes for the deamination of an aminothiazole group to give a thiazole group are known and are described in J. Chem. Soc, 1973, 541, (J. Cadogan and G. Molina).

Advantageously, the removal of $R^1$, when $R^1$ is a protecting group such as N-acyl, and the hydrolysis of the ester group can be carried out in a single step, for example by refluxing with excess base, such as sodium hydroxide, in an aqueous solvent system such as aqueous dioxan.

Y may be any suitable group, but it is preferred that Y be an α-halo acetyl group (or an acetyl group which can be α-halogenated), the conversion of which may be effected by condensation with optionally N-acylated thiourea. The condensation reaction is typically carried out at elevated temperatures in an inert solvent such as dimethyl formamide.

Aldehydes of formula RCHO can be obtained by deetherifying a corresponding enol ether of formula $R=CHOR^5$ wherein $R^5$ is alkyl such as methyl.

Compounds of formula $R=CHOR^5$ may be prepared by an analagous procedure to that outlined in EP-A-0 159 784.

Certain of the compounds of formula (III) are novel, and these novel compounds and their derivatives also form a part of the present invention.

The present invention also provides a pharmaceutical composition which comprises a compound of formula (I) or a pharmaceutically acceptable salt or in vivo hydrolysable ester thereof and a pharmaceutically acceptable carrier. The compositions of the invention include those in a form adapted for oral, topical or parenteral use and may be used for the treatment of the infection in mammals including humans.

The antibiotic compounds according to the invention may be formulated for administration in any convenient way for use in human or veterinary medicine, by analogy with other antibiotics, and the invention therefore includes within its scope a pharmaceutical composition comprising a compound of formula (I) above together with a pharmaceutical carrier or excipient.

The composition may be formulated for administration by any route, such as oral, topical or parenteral. The compositions may be in the form of tablets, capsules, powders, granules, lozenges, creams or liquid preparations, such as oral or sterile parenteral solutions or suspensions.

The topical formulations of the present invention may be presented as, for instance, ointments, creams or lotions, eye ointments and eye or ear drops, impregnated dressings and aerosols, and may contain appropriate conventional additives such as preservatives, solvents to assist drug penetration and emollients in ointments and creams.

The formulations may also contain compatible conventional carriers, such as cream or ointment bases and ethanol or oleyl alcohol for lotions. Such carriers may be present as from about 1% up to about 98% of the formulation. More usually they will form up to about 80% of the formulation.

Tablets and capsules for oral administration may be in unit dose presentation form, and may contain conventional excipients such as binding agents, for example syrup, acacia, gelatin, sorbitol, tragacanth, or polyvinylpyrrolidone: fillers, for example lactose, sugar, maize-starch, calcium phosphate, sorbitol or glycine, tabletting lubricants, for example magnesium stearate, talc, polyethylene glycol or silica; disintegrants, for example potato starch; or acceptable wetting agents such as sodium lauryl sulphate. The tablets may be coated according to methods well known in normal pharmaceutical practice. Oral liquid preparations may be in the form of, for example, aqueous or oily suspensions, solutions, emulsions, syrups or elixirs, or may be presented as a dry product for reconstitution with water or other suitable vehicle before use. Such liquid preparations may contain conventional additives, such as suspending agents, for example sorbitol, methyl cellulose, glucose syrup, gelatin, hydroxyethyl cellulose, carboxymethyl cellulose, aluminium stearate gel or hydrogenated edible fats, emulsifying agents, for example lecithin, sorbitan monooleate, or acacia; non-aqueous vehicles (which may include edible oils), for example almond oil, oily esters such as glycerine, propylene glycol, or ethyl alcohol; preservatives, for example methyl or propyl p-hydroxybenzoate or sorbic acid, and, if desired, conventional flavouring or colouring agents.

Suppositories will contain conventional suppository bases, e.g. cocoa-butter or other glyceride.

For parenteral administration, fluid unit dosage forms are prepared utilizing the compound and a sterile vehicle, water being preferred. The compound, depending on the vehicle and concentration used, can be either suspended or dissolved in the vehicle. In preparing solutions the compound can be dissolved in water for injection and filter sterilised before filling into a suitable vial or ampoule and sealing. Advantageously, agents such as a local anaesthetic, preservative and buffering agents can be dissolved in the vehicle. To enhance the stability, the composition can be frozen after filling into the vial and the water removed under vacuum. The dry lyophilized powder is then sealed in the vial and an accompanying vial of water for injection may be supplied to reconstitute the liquid prior to use. Parenteral suspensions are prepared in substantially the same manner except that the compound is suspended in the vehicle instead of being dissolved and sterilization cannot be accomplished by filtration. The compound can be sterilised by exposure to ethylene oxide before suspending in the sterile vehicle. Advantageously, a surfactant or wetting agent is included in the composition to facilitate uniform distribution of the compound.

The compositions may contain from 0.1% by weight, preferably from 10–60% by weight, of the active material, depending on the method of administration. Where the composition comprise dosage units, each unit will preferably contain from 50–500 mg of the active ingredient. The dosage as employed for adult human treatment will preferably range from 100 to 3000 mg per day, for instance 1500 mg per day depending on the route and frequency of administration. Such a dosage corresponds to 1.5 to 50 mg/kg per day. Suitably the dosage is from 5 to 20 mg/kg per day.

No toxicological effects are indicated when a compound of formula (I) is administered in the above-mentioned dosage range.

Compounds of the present invention are characterised by increased stability to β-lactamase producing organisms when compared to synthetic penicillins in commercial use such as amoxycillin.

The compound of the invention of formula (I) may therefore be used as the sole therapeutic agent in compositions of the invention or may be used in combination with other antibiotics or with a β-lactamase inhibitor.

Advantageously the compositions also comprise a compound of formula (V) or a pharmaceutically acceptable salt or ester thereof:

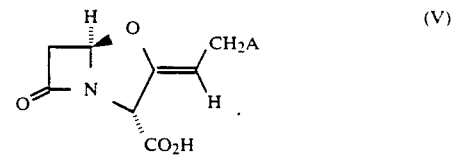

wherein A is hydroxyl; substituted hydroxyl; thiol; a group of formula $SO_2R^6$ wherein $R^6$ is $C_{1-6}$ alkyl; substituted thiol; amino; mono- or di-hydrocarbyl substituted amino; mono- or di-acylamino; an optionally substituted triazolyl group; or an optionally substituted tetrazolyl group as described in EP 0 053 893.

A further advantageous composition comprises an antibiotic compound according to the invention and a pharmaceutically acceptable carrier or excipient together with a β-lactamase inhibitor of formula (VI) or a pharmaceutically acceptable salt or in vivo hydrolysable ester thereof:

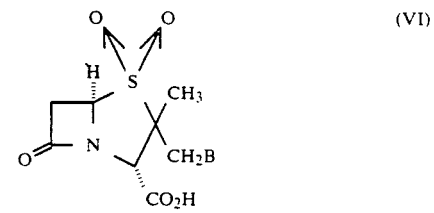

wherein B is hydrogen, halogen or a group of formula:

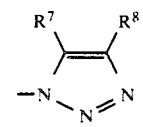

in which $R^7$ and $R^8$ are the same or different and each is hydrogen, $C_{1-6}$ alkoxycarbonyl, or carboxy or a pharmaceutically acceptable salt thereof.

Further suitable β-lactamase inhibitors include 6-alkylidene penem of formula (VII) below:

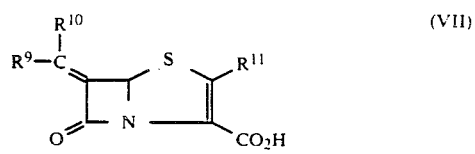

or a pharmaceutically acceptable salt or in vivo hydrolysable ester thereof, wherein $R^9$ and $R^{10}$ are the same or different and each represents hydrogen, or a $C_{1-10}$ hydrocarbon or heterocyclic group optionally substituted with a functional group; and $R^{11}$ represents hydrogen or a group of formula $R^a$ or $-SR^a$ where $R^a$ is an optionally substituted $C_{1-10}$ hydrocarbon or heterocyclic group, as described in EP-A-0 041 768.

Other suitable β-lactamase inhibitors include 6β-bromopenicillanic acid and salts and in vivo hydrolysable esters thereof and 6β-iodopenicillanic acid and salts and in vivo hydrolysable esters thereof.

Such compositions of this invention comprising a β-lactamase inhibitor are formulated in conventional manner.

The present invention also includes a method of treating bacterial infections in humans and animals which comprises the administration of a therapeutically effective amount of an antibiotic compound of this invention.

Antibiotic compounds of the present invention are active against a broad range of bacteria, in particular they are useful for treatment of respiratory tract and urinary tract infections in humans and mastitis in cattle. It should be stressed that a particular advantage of certain compounds of the invention is their stability to β-lactamase enzymes and they are therefore effective against β-lactamase-producing organisms.

The antibiotic compounds of the present invention are active against both Gram-negative and Gram-positive organisms including *E.coli*, in particular ESS and NCTC 10418; *H.influenzae*, in particular Q1 and NEMC 1; *S.aureus* such as Oxford, Russell and MB 9; *S.pyogenes* such as CN10; *S.agalactiae* such as 2798; *S.pneumoniae* such as PU7 and 1761; and *B.catarrhalis* such as Ravasio.

The following Example illustrates the preparation of the compounds of the present invention.

EXAMPLE 1

Sodium 6β-[Z-[2-(2-aminothiazol-4-yl)-3-(tetrahydro-4H-pyran-4-yl)₁propenamido₁penicillanate (a) 4-(Methoxymethylene)tetrahydro-4H-pyran This compound was prepared by a variation of a published procedure [Eur.Pat.Appl.No. 0159784 (to Upjohn Co.)]. Methoxymethyltriphenylphosponium chloride (5.47g) was suspended in anhydrous tetrahydrofuran (15ml) and stirred under argon at 0° C. 1M Lithium hexamethyldisilazide in the same solvent (16.0 ml) was added via a syringe and stirring continued at 0°-20° C. for 0.5 h. The resulting dark red near solution was cooled to −25° C. and tetrahydro-4H-pyran-4-one (1.40 ml) was added. The mixture was allowed to regain ambient temperature and stirred for a further 16 h, then poured into water and extracted twice with ether. The total organic extract was washed twice with water and once with brine, dried and evaporated to dryness. The residue was treated with ether: n-hexane (1:3) and cooled, then the crystalline solid was filtered off and the filtrate was evaporated. After repeating this process once the residue was subjected to Kugelrohr distillation to give the enol ether (1.07g); $\nu_{max}$(CHCl₃) 1690, 1455, and 1430cm⁻¹; δ(CDCl₃, 60 MHz) 2.1, 2.4 (4H, 2t), 3.65 (3H, s), 3.70 (4H, m), and 5.95 (1H, brs). (Found: C, 65.4; H, 9.6. C₁₇H₁₂O₂ requires C, 65.6; H, 9.4%).

b) Tetrahydro-4H-pyran-4-carboxaldehyde 4-(Methoxymethylene)tetrahydro-4H-pyran (0.9g) in a mixture of water (5 ml) and tetrahydrofuran (5 ml) was stirred at ambient temperature with toluene-4-sulphonic acid hydrate (1.90g) for 6.5 h. After this time no enol ether could be detected by t.l.c. The mixture was treated with saturated aqueous NaHCO₃ (15 ml), saturated with sodium chloride and extracted with four portions of dichloromethane. The combined organic extracts were dried and evaporated to give the title aldehyde (0.72g) (V.Prelog and E.Cerkovnikov, *Coll.-Czech.Chem.Comm.*, 1935, 7, 430); δ(CDCl₃, 60 MHz) 1.85 (4H, m), 2.4 (1H, m), 3.2–4.2 (4H, m), and 9.8 (1H, brs).

c) Methyl Z-[2-(2-acetamidothiazol-4-yl)-3-(tetrahydro-4H-pyran-4-yl)propenoate

Tetrahydro-4H-pyran-4-carboxaldehyde (0.72g) was mixed with methyl 4-chloroacetoacetate (0.95g) and stirred under argon at −10° C. in the presence of piperidine (2 drops). After 4 h the reaction mixture was diluted with ethyl acetate and washed with ice-cold 1M hydrochloric acid (3×), water and brine. Evaporation of the dried extract gave a yellowish oil which was chromatographed on silica gel to remove traces of starting materials. The resulting oil (0.71g) in dry DMF (5 ml) was heated with N-acetyl thiourea (0.32g) at 90°-95° C. for 1.5 h. The reaction mixture was cooled, poured onto ice-water and extracted twice with ethyl acetate, then the combined organic extracts were washed with water (3x), brine, dried and evaporated to give crude product (0.68g). Chromatography on silica gel eluting with ethyl acetate-hexane mixtures gave, after pooling and evaporation of appropriate fractions, the title Z-ester (150mg); $\nu_{max}$ (KBr) 3236, 3189; 1726, 1660, 1551, and 1500(w)cm⁻¹; δ(CDCl₃, 250 MHz) 1.68 (4H, m), 2.24 (3H, s), 2.89 (1H, m), 3.40–4.10 (4H, m), 3.88 (3H, s), 6.59 (1H, d, J=10 6.95. (1H, s), and 9.29 (1H, br s). The n.m.r. spectrum showed the presence of other materials which were not u.v. absorbing, but the aminothiazole constituent was the desired compound. (Found: M, 310.0995. C₁₄H₁₈N₂O₄S requires M, 310.0987).

(d) Z-[2-(2-aminothiazol-4-yl)-3-(tetrahydro-4H-pyran-4-yl)]propenoic acid

Methyl Z-[2-(2-acetamidothiazol-4-yl)-3-(tetrahydro-4H-pyran-4-yl)]propenoate (111 mg) in dioxan (3 ml) was heated with five equivalents of 1M sodium hydroxide at 90°-95° C. After 6 h the reaction mixture was cooled and evaporated to dryness, then the residue was dissolved in water and washed twice with ether: ethyl acetate (1:1), backwashing each time with a little water. The total aqueous phase was acidified to pH2 using 2M hydrochloric acid, saturated with sodium chloride and extracted with three portions of tetrahydrofuran. The total organic extract was dried and evaporated to give crude material (102mg) which was purified by silica gel chromatography, eluting with ethyl acetate-isopropanol-water mixtures. Appropriate fractions were combined and evaporated to give the title acid (56mg); $\nu_{max}$ (KBr) 1630(sh), 1569, 1530(sh), and 1413cm⁻¹; δ[(CD₃)₂SO, 250 MHz]1.20-1.65 (4H, 2m), 2.78 (1H, m), 3.30, 3.83 (4H, 2m), 5.94 (1H, d, J=10Hz), 6.45 (1H, s), and 6.95 (2H, br s); m/e 255 (MH+).

(e)

Sodium 6β-[Z-[2-(2-aminothiazol-4-yl)-3-(tetrahydro-4H-pyran-4-yl)]propenamido]penicillanate Z-[2-(2-Aminothiazol-4-yl)-3-(tetrahydro-4H-pyran-4-yl)]propenoic acid (49mg) and 1-hydroxybenzotriazole monohydrate (33mg) were stirred in dry DMF (1.5 ml) at 0° C. whilst N,N'-dicyclohexylcarbodiimide (43mg) was added. The mixture was allowed to warm to room temperature and stirred under argon for 2.75 h. T.l.c. showed active ester to have formed. The mixture was filtered into a stirring solution of 6-aminopenicillanic acid (49mg) and 1N NaOH (0.23 ml) in H$_2$O (1 ml) (filtered solid was washed with fresh DMF). The mixture was stirred at room temperature for 2.5 h, when t.l.c. showed reaction to be complete. The mixture was filtered, the precipitate was washed with water and tetrahydrofuran and the combined filtrates were evaporated to near dryness. The residue was dissolved in water containing saturated aqueous sodium hydrogen carbonate solution (1 ml) and washed twice with ethyl acetate: ether (1:1), backwashing each time with a little water. The combined aqueous extracts were acidified to pH2 using 2MHCl, saturated with sodium chloride, and extracted twice with ethyl acetate and twice with tetrahydrofuran. The combined organic extracts were dried and evaporated to give crude product (140mg). Chromatography on HP20SS, eluting with water-acetone mixtures, followed by concentration of appropriate fractions to low volume, adjustment to pH 6.5 and freeze drying gave the title penicillin (18mg); $\nu_{max}$(KBr) 1763, 1660(sh), 1603 and 1526cm$^{-1}$; δ(D$_2$O, 250 MHz) 1.50, 1.59 (6H, 2s), 1.40–1.75 (4H, 2m), 2.55 (1H,m), 3.51, 3.93 (4H, 2m), 4.22 (1H, s), 5.61 (2H, dd), 6.12 (1H, d, J=10Hz), and 6.49 (1H, s); m/e 475 (MH+), 453 (M-Na+H+).

EXAMPLE 1

(f)

1-Acetoxyethyl-6β-[Z-2-(2-aminothiazol-4-yl)-3-(tetrahydropyran-4-V])propenamido penicillanate.

Z-[2-(2-aminothiazol-4-yl-3-(tetrahydropyran-4-yl)propenoic acid (250mg) was coupled to 1-acetoxyethyl-6-aminopenicillanate (474mg; as the toluene-4-sulphonate) using the mesyl chloride procedure described in Example 2g. Chromatography of the residue after work up on silica gel using ethyl acetate as eluent gave the title product as a mixture of epimers (80mg). $\nu_{max}$ (CHCl$_3$) 3400, 3000, 1770, 1675, 1605cm$^{-1}$; δ(CDCl$_3$, 250 MHz) inter alia 2.09, 2.1 (3H, 2S, OCH(CH$_3$)$_0$), 2.8–3.1 (1H, m, tetrahydropyran CH), 4.41 4.46 (1H, 2S, 3-H), 5.00 (2H, s,NH$_2$), 6.27 (1H, d, J=10Hz, acrylic H), 6.47 (1H, s, 5$^1$-H), 6.8–6.95 (1H, m, OCH(CH$_3$)$_0$ m/e 539 (MH+).

EXAMPLE 2

Sodium 6β-[Z-2-aminothiazol-4-yl)-3-(tetrahydrothiapyran-4-yl)$_1$propeneamidopenicillanate (a) 4-(Methoxymethylene)tetrahydrothiapyran Methoxymethyltriphenylphosphonium chloride (13.7g) in dry tetrahydrofuran (40 ml) was stirred under argon at 0° whilst a solution of potassium t-butoxide (4.48g) in dry tetrahydrofuran (40 ml) was added dropwise. The temperature was maintained at 0° during the addition and then stirred for a further 30 min at 0° The resulting dark red solution was then cooled to −25° and tetrahydrothiapyran-4-one (4.5g) added in one portion. The mixture was allowed to regain ambient temperature and then stirred at room temperature overnight. Water was now added and the solution extracted twice with ether. After drying the extracts over anhydrous magnesium sulphate they were evaporated to give a colourless oil from which a white solid precipitated. The residue was treated with ether-hexane (1:3), the crystalline solid filtered off and the filtrate evaporated. After repeating this process three times the residue was subjected to Kügelrohr distillation to give the enol ether as a colourless liquid (2.1 g).

(b) Tetrahydrothiapyran-4-carboxaldehyde 4-(Methoxymethylene)tetrahydrothiapyran (2.1 g) in a mixture of water (10 ml) and tetrahydrofuran (10 ml) was stirred at room temperature with toluene-4-sulphonic acid hydrate (3.8g) for 18 hr. Saturated aqueous sodium bicarbonate was added carefully and then the basic solution was extracted four times with dichloromethane. The combined organic extracts were dried over anhydrous magnesium sulphate and evaporated. Kügelrohr distillation (water pump) gave the title compound as a colourless liquid (1.55g).

(c)

2-(4-Tetrahydrothiapyranylidene)-3-oxo-4-chlorobutyric acid, methyl ester.

Tetrahydrothiapyran-4-carboxaldehyde (1.5g) in ethyl acetate (10 ml) was treated with methyl-4-chloroacetoacetate (1.5g), 4A sieve (3g) and the mixture cooled in an ice-bath. Piperidine (3 drops) and acetic acid (3 drops) were now added and the mixture stirred at 0-5° for 45 min. Excess ethyl acetate was added and the organic solution washed with 1M hydrochloric acid. After washing the extracts with water they were dried over anhydrous magnesium sulphate and evaporated to give a colourless oil. Chromatography o silica gel using ethyl acetate-hexane mixtures gave the title compound mixture Z/E (1:2)) as a colourless oil (2g). $\nu_{max}$(CHCl$_3$) 1720 and 1630 cm$^{-1}$; δ(CDCl$_3$) inter alia 3.82(s) and 3.87(s), 6.84 (d, J=10Hz) and 6.94 (d, J TM 10Hz) m/e 262 (M+).

(d)

Methyl-Z-2-(2-acetamidothiazol-4-yl)-3-(tetrahydrothiapyran-4-yl)]propenoate.

The product from Example 2c. (2g) in dry DMF (12 ml) was treated with N-acetylthiourea (0.91g) and the mixture heated at 90° for 3 hr. Solution was cooled, diluted with ethyl acetate and the organic solution washed thoroughly with water. After drying over anhydrous magnesium sulphate the extracts were evaporated to give an orange solid. Chromatography of the residue on silica gel using ethyl acetate-hexane mixtures gave the title Z-ester as a colourless solid (0.62g); $\nu_{max}$(CHCl$_3$) 3420 1700, 1580 and 1540 cm$^{-1}$; δ[CDCl$_3$, 250 MHz] 1.5–1.8 (2H, m), 1.9–2.2 (2H, m), 2.25 (3H, s), 2.5–2.9 (5H, m), 3.88 (3H, s), 6.56 (1H, d, J=10Hz), 6.96 (1H, s), 9.03 (1H, brs) m/e 326 (M+).

(e)

Z-[2-(2-aminothiazol-4-yl)-3-(Tetrahydrothiapyran-4-yl)propenoic acid.

Methyl Z-[2-(2-acetamidothiazol-4-yl)-3-(tetrahydrothiapyran-4-yl)]propenoate (600mg) in a mixture of dioxan (8 ml) and water (8 ml) was treated with sodium hydroxide (500mg) and the mixture heated at 90° for 3 hr. The solution was cooled, diluted with water and the mixture extracted with ethyl acetate. The aqueous solution was acidified to pH$_2$ using 1M hydrochloric acid and the solution thoroughly extracted with ethyl acetate. After drying over anhydrous magnesium sulphate the organic extracts were evaporated to give the title acid as an orange foam (320mg), $\nu_{max}$(KBr) 1700(sh), 1630, 1560, 1530 and 1420 cm$^{-1}$. Δ[(CD$_3$)$_2$SO, 250 MHz] 1.3–1.6 (2H, m), 1.8–2.1 (2H, m), 2.4–2.8 (5H, m), 6.26 (1H, d, J=10Hz), 6.42 (1H, s), 7.06 (2H, s).

(f) Sodium 6β-[Z-2-(2-aminothiazol-4-yl)-3-(tetrahydropyran-4-yl)]propenamido penicillanate.

Z-[2-(2-aminothiazol-4-yl)-3-(tetrahydrothiapyran-4-yl)]propenoic acid (170mg) was treated with di-isopropylethylamine (0.15 ml) and the mixture cooled to −40°. Methanesuphonyl chloride (0.075 ml) was added and the mixture stirred at −40° to −30° for 1 hr. A solution of 6-aminopenicillanic acid (152mg) in water (5 ml) containing triethylamine (0196 ml) was added at this temperature and subsequently the mixture was stirred at 0° for a further 1½ hr. The solution was diluted with water, the pH adjusted to 7.5 using aqueous sodium bicarbonate solution and then extracted with ethyl acetate. The aqueous solution was adjusted to pH 2.5 using 1M hydrochloric acid and extracted with ethyl acetate. The combined organic extracts were evaporated and the residue chromatographed on HP20SS eluting with acetone-water mixtures. Appropriate fractions were combined and freeze-dried to give the title penicillin (170mg) $v_{max}$(KBr) 1765, 1660(sh), 1605 and 1525 cm$^{-1}$; δ((CD$_3$)$_2$SO), 250 MHz) inter alia 1.45, 1.52 (6H, 2s), 3.82 (1H, s) 5.35–5.46 (2H, m), 6.02 (1H, d, J=10Hz), 6.24 (1H, s), 7.03 (S, 2H), 8.96 (1H, s, J=7Hz).

(g) 1-Acetoxyethyl 6B-Ż-2(2-aminothiazol-4-yl)-3-tetrahydrothiapyran-4-yl)]propenamido penicillanate.

Z-[2-aminothiazol-4-yl)-3-(tetrahydrothiapyran-4-yl)propenoic acid (230mg) in dry DMF (5 ml) was cooled to 0° and treated with di-isopropylethylamine (0.2 ml). This solution was then cooled to −40° , methanesulphonyl chloride added and the mixture stirred at 0°-40° for 30 min. A solution of 6-aminopenicillanate acid axetil ester [prepared in situ from 6-APA axetil ester−toluene-4-sulphonic acid (570mg), triethylamine (0.33 ml) and DMF(5 ml)]in DMF (5 ml) was added at −40° and the stirring then continued at 0° for another 30 minutes. Excess ethyl acetate was added, the organic solution washed thoroughly with water and dried over anhydrous magnesium sulphate. Evaporation and chromatography of the residue on silica gel using ethyl acetate as eluant gave the title compound as a colourless foam (300 mg)$v_{max}$(CDCl$_3$) 1685(sh), 1670, 1680, 1600 and 1500 cm$^{-1}$, δ(CDCl$_3$, 250 MHz) inter alia 1.53, 1.56, 1.59, 1.62, 1.66 (9H, 5s, OCH(CH$_3$)O, 2×CH$_3$), 2.09, 2.1 (3H, s+s, CH$_3$COO), 4.42, 4.46 (1H, s+s, 3-H), 5.01 (2H, brs, NH$_2$), 5.5-5.7 (1H, m, 6-H), 5.75–5.9 (1H, m, 5-H), 6.75–6.95 (1H, m, OCH(CH$_3$)O, 7.3–7.45 (1H, m, CONH) m/e 577 (MNa+).

EXAMPLE 3

Sodium 6γ-[Z-2-(2-aminothiazol-4-yl)-3-(tetrahydropyran-3-yl)$_1$-propenamido penicillanate

(a) 2-(3-Tetrahypyranylidine)-3-oxo-4-chlorobutyric acid, methyl ester

Methyl-4-chloroacetoacetate (1.2 ml) in dry benzene (30 ml) was treated with tetrahydropyran-3-carboxaldehyde (1.2g), piperidine (10 drops) acetic acid (20 drops) and the mixture heated under Dean and Stark conditions for 1 hr. The solution was allowed to cool, diluted with ethyl acetate and the organic solution washed with water. After drying over anydrous magnesium sulphate the solvent was evaporated to give a pale yellow oil. Chromatography of the residue a silica gel using ethyl acetate-hexane (1:4) as eluent gave the title product as a pale yellow oil (1.6g) as a 2:3 mixture of Z/E isomers. δ(CDCl$_3$, 250 MHz) inter alia 3.82, 3.88 (3H, 2s,— CO$_2$CH$_3$), 4.32, 4.41 (2H, 2s, ClCH$_2$), 6.92, 7.00 (1H, 2d, acrylic —H) m/e 247 (MH+) 264 (MNH$_4$+).

(b) Methyl Z-2-(2-acetamidothiazol-4-yl)-3-(tetrahydropyran-3-yl]propenoate The product from Example 3a (1.55g) in dry DMF (10 ml) was treated with N-acetylthiourea (0.75g) and the mixture heated at 95° for 3 hr. Solution was cooled, poured into excess ethyl acetate and the organic solution washed thoroughly with water. After drying over anhydrous magnesium sulphate the solution was evaporated. Chromatography of the residue on silica gel using ethyl acetate-hexane (1:1) as eluent gave the title product as a white solid (540mg) $v_{max}$(CHCl$_3$) 3420 00, 1605 and 1540 cm$^{-1}$; δ(CDCl$_3$, 250 MHz) inter alia 2.25 (3H, s, CH$_3$CONH), 3.88 (3H, s, CO$_2$CH$_3$), 6.56 (1H, d, acrylic-H̲), 6.97 (1H, s, thiazole 5-H̲), 9.02 (1H, brs, CH$_3$CONH̲) m/e 310 (M+).

(c) Z-2-(2-aminothiazol-4-yl)-3-(tetrahydropyran-3-yl)]propenoic acid

Methyl Z-[2-(2-acetamidothiazol-4-yl)-3-(tetrahydropyran-3-yl)], propenoate (390mg) was hydrolysed as in Example 1d to give the title acid a buff foam (180mg). δ[(CD$_3$)$_2$SO, 250 MHz]inter alia 6.29 (1H, d, acrylic-H), 6.55 (1H, s, thiazol 5-H).

(d) Sodium 6β-[Z-2-(2-aminothiazol-4-yl)-3-(tetrahydropyran-3-yl)$_1$propenamido penicillanate.

The product from the previous Example 3c (170mg) was coupled to 6-aminopenicillanic acid (172mg) using the mesyl chloride route described in Example 2f. Chromatography of the worked-up product on HP20SS, eluting with acetone-water mixtures, followed by concentration of the appropriate fraction to a low volume and freeze drying gave the title penicillin (70 mg). $v_{max}$(KBr) 1770, 1660, 1620 an 1525 cm$^{-1}$. δ[(CH$_3$)$_2$SO, 250 MHz]inter alia 1.44, 1.51 (6H, 2s; 2×CH$_3$), 3.82 (S, 1H, 3-H), 5.3–5.48 (2H, m, 5-H̲, 6-H̲), 6.27, 6.28 (1H, 2s, thiazole 5-H̲).

EXAMPLE 4

Sodium 6B-[Z-2-(2-aminothiazol-4-yl)-3-(tetrahydropyran-2-yl)}propenamide penicillanate

(a) Ethyl 2-(2-N,N-dimethylmethyleneaminothiazol4-yl)-3-(tetrahydropyran-2-yl)$_1$crocenoate Diphenylamine (2.3g) in dry tetrahydrofuran (30 ml) under an argon atmosphere was cooled to −20° C. and treated with butyl lithium (5.8 ml of a 2M solution in hexane). The coolant bath was removed and the mixture stirred for 10 min. The solution was recooled to −20° and ethyl-2-[2-N,N-dimethylmethyleneaminothiazol-4-yl]acetate in dry TMF (15 ml) added dropwise with stirring. After stirring at −20° for 10 min, tetrahydropyran-2-carboxaldehyde (2g) in dry THF (10 ml) was added to the reddish coloured solution and the mixture stirred at −20° for a further 15 min. Acetic anhydride (4.8 ml) was now added and the reaction stirred at ambient temperature for 45 min. The reaction mixture was poured into an ethyl acetate-saturated aqueous sodium chloride solution, the organic phase separated and washed successively with, saturated aqueous sodium bicarbonate, water and finally brine. After drying over anhydrous magnesium sulphate the solvent was evaporated to give a yellow oil. The oil was dissolved in dichloromethane (40 ml), treated with 1,8-Diazabicyclo[5.4.0]undec 7-ene (3 ml) and the mixture stirred at room temperature overnight. The mixture was evaporated and the residue chromatographed on silica gel using ethyl acetate-hexane (1:4) as eluant to give the title acrylate (1:1 mixture Z/E) as a brown oil (1.6g) $v_{max}$(CHCl$_3$) 1705 and 1620 cm$^{-1}$. $\delta$(CDCl$_3$, 250 MHz) inter alia 1.2–1.45 (m, 3H, CO$_2$CH$_2$CH$_3$), 4.15–4.45 (2H, m, CO$_2$CH2CH$_3$), 6.88, 6.95 (1H, 2d, J10.5Hz, Z and E acrylate-H), 8.26, 8.29 (1H, 2s, amidine CH) m/e 337 (M$^+$).

(b) Ethyl Z-2-(2-formamidothiazol-4-yl-3-(tetrahydropyranyl-2-yl)propenoate.

The product from Example 4a (800 mg) was treated with formic-acetic anhydride (10 ml) and the mixture stirred at RT for 1 hr. The solution was then poured carefully into a stirred mixture of 10% aqueous sodium carbonate and ethyl acetate. The organic layer was further washed, successively with 10% aqueous sodium carbonate and water, and dried over anhydrous magnesium sulphate. Evaporation and chromatography of the residue on silica gel using ethyl acetate-hexane (1:1) as eluant gave the title product as a colourless oil (200 mg). $v_{max}$(CHCl$_3$) 1700 and 1545 cm$^{-1}$. $\delta$(CDCl$_3$, 250 MHz) inter alia 1.37 (3H, t, CO$_2$CH$_2$CH$_3$), 4.15–4.5 (3H, m, —CO$_2$CH$_2$CH$_3$ and tetrahydropyranyl-CH), 6.65 (1H, d, acrylic-H), 7.1 (s, 1H, thiazol 5-H), 8.56 (1H, s, —NHCHO), 10.43 (1H, brs, —NHCHO).

(c) Z-2-(2-aminothiazol-4-yl)-3-(tetrahydropyran-2-yl)propenic acid.

Ethyl-Z-([2-(2-formamidothiazol-4-yl)-3-(tetrahydropyran-2-yl])propenoate (120 mg) in a mixture of dioxan (7 ml) and water (7 ml) was treated with sodium hydroxide (77 mg) and heated at 100° for 30 min. Solution was cooled, acidified to pH 2.5 using 1M hydrochloric acid and extracted thoroughly with ethyl acetate. After drying over anhydrous magnesium sulphate the solution was evaporated and the residue chromatographed on silica gel using ethyl acetate-isopropanol-water (7:2:1) to give the title product as a yellow foam (24 mg) $\delta$[(CH$_3$)$_2$SO, 250 MHz]6.30 (1H, d, acrylic —H), 6.50 (1H, s, thiazole 5-H), 7.02 (2H, s, —NH$_2$).

(d) Sodium 6$\beta$-Z-2-(2-aminothiazol-4-yl)-3-(tetrahydropyran-2-yl)$_1$propenamido penicillanate The product from Example 4c (19 mg) was coupled to 6-aminopenicillanic acid (19 mg) using the active ester procedure as described in Example 1e. After the conventional work-up procedure the crude sodium salt was applied to an HP20SS column. Chromatography, eluting with acetone-water mixtures, gave the title compound (12 mg) after freeze drying of the appropriate fractions. $v_{max}$(KBr) 1770, 1665, 1620 and 1530 cm$^{-1}$. $\delta$[D$_2$O, 250 MHz]4.21, 4.22 (1H, 2H, 3-H), 5.45-5.65 (2H, m, 5-H and 6-H), 6.17 (1H, d, acrylic-H), 6.59, 6.61 (1H, 2s, 5$^1$-H).

EXAMPLE 5

Sodium 6$\beta$-[Z-2-(2-aminothiazol-4-yl)-3-(tetrahydrothiophen-3-yl)]propenamido penicillanate (a) Tetrahydrothiophene-3-carboxaldehyde 2,5-Dihydrothiophene-3-carboxaldehyde (3g) in ethyl (150 ml) was treated with decolourising charcoal (5g) and the suspension stirred for 30 min. The charcoal was filtered off and the solution shaken with a suspension of 10% Pd-C (3g) under 1 atmosphere of hydrogen for 1½ hr. The catalyst was filtered off and washed with ethyl acetate. Combination of the filtrates and evaporation gave the title product as a colourless oil (2.73g) $\delta$(CDCl$_3$, 250 MHz) 1.8–3.5 (m, tetrahydrothiophene-4×CH$_2$l), 9.67 (1H, s, —CHO).

(b) 2-(3-Tetrahydrothiophenylidene)-3-oxo-4-chlorobutyric acid, methyl ester.

Methyl-4-chloroacetoacetate (2.84g) in dichloromethane (20 ml) containing 4A molecular sieve (5g) was treated with tetrahydrothiophene-3-carboxyaldehyde (2.2g), piperidine (10 drops), acetic acid (10 drops) and the mixture stirred at ambient temperature for 45 min. The solution was diluted with dichloromethane and the organic solution washed with water and brine. After drying over anhydrous magnesium sulphate the solvent was evaporated. Chromatography of the residue on silica gel using ethyl acetate-hexane (1:3) as eluant gave the title product as a 3:2 mixture of Z/E isomers (1.15g).

(c) Methyl Z-2-(2-acetamidothiazol-4-yl)-3-(tetrahydrothiophene-3-V111propenoate The product from Example 5b (1.15g) in dry DMF (15 ml) was treated with N-acetylthiourea (0.55g) and the mixture heated at 95° for 1¾ hr. Solution was cooled, diluted with ethyl acetate and the resulting organic solution washed thoroughly with water. After drying over anhydrous magnesium sulphate solvent was evaporated to give a brown oil. Chromatography of the residue on silica gel using ethyl acetate-hexane (1:1) as eluant gave the title product as a beige solid (0.55g) $v_{max}$(nujol) 1720, 1690, 1640, 1610 and 1550 cm$^{-1}$; $\delta$(CDCl$_3$, 250 MHz) inter alia 2.26 (3H, s, CH$_3$CONH), 3.88 (3H, s, CO$_2$CH$_3$), 6.64 (1H, d, acrylic -H), 6.89 (1H, s, thiazole 5-H), 7.94 (1H, br.s, CH$_3$CONH).

(d) Z-2-(2-aminothiazol-4-yl)-3-(tetrahydrothiophen-3-yl)$_1$propenoic acid.

Methyl Z-[2-(acetamidothiazol-4-yl)-3-(tetrahydrothiophen-3-yl)]propenoate (0.55g) was hydrolysed as in Example 1d. Work-up gave the title acid as a beige solid (0.32g).

(e) Sodium 6$\beta$-[Z-2-(2-aminothiazol-4-yl)-3-(tetrahydrothiophen-3-yl)$_1$propenamido penicillanate.

The product from Example 5d (0.32g) was coupled to 6-aminopenicillanic acid (324g) using the active ester procedure as described in Example 1e. After a conventional work-up procedure the crude sodium salt was applied to an HP20SS column. Chromatography, eluting with acetone-water mixtures, gave the title compound (110 mg) after freeze drying the appropriate fractions. $\nu_{max}$(KBr) 1760, 1660 and 1605 cm$^{-1}$; m/e 455[(M-Na+H]476 (MH+).

EXAMPLE 6

Sodium 6β-[Z-2-(2-aminothiazol-4-yl)-3-(tetrahydrothiapyran-3-yl)₁propenamido penicillanate (a) Tetrahydrothiapyran-3-carboxaldehyde 3-Formyl-5,6-dihydro-2-H-thiopyran (3g) (prepared by the procedure described in U.S. Pat. No. 4,629,799) in ethyl acetate (50 ml) containing a suspension of 10% Pd-C (3g) was shaken under 1 atmosphere of hydrogen for 2½ hr. The catalyst (3g) was replaced and the mixture shaken for a further 1½ hrs. Uptake of hydrogen was now very rapid. The catalyst was filtered off (celite), washed with ethyl acetate and the organic filtrate evaporated to give the title aldehyde as a pale yellow oil (2.65g) $\nu_{max}$(film) 1720 and 1680 cm$^{-1}$.

(b) 2-(3-Tetrahydrothiapyranylidene)-3-oxo-4-chlorobutyric acid methyl ester

Methyl-4-chloroacetoacetate (3g) in benzene (50 ml) was successively treated with tetrahydrothiapyran-3-carboxaldehyde (2.5g), piperidine (10 drops), acetic acid (20 drops) and then heated under Dean and Stark conditions for 2 hr. After cooling, the mixture was diluted with ethyl acetate and the organic solution washed well with water. The solution was dried over anhydrous magnesium sulphate and evaporated. Chromatography of the residue on silica gel using ethyl acetate-hexane (1:3) as eluant gave the title acrylate a pale yellow oil (2.7g) as an approximate 1:1 mixture of Z and E isomers. $\nu_{max}$ (film) 1710 and 1620 cm$^{-1}$; δ(CDCl$_3$, 250 MHz) inter alia 3.82, 3.88 (3H, 2s, —CO$_2$CH$_3$), 4.37, 4.41 (2H, 2s, ClCH$_2$), 6.94, 7.04 (1H, 2d, 'Z' and 'E' acrylate -H); m/e 262 (M+).

(c) Methyl Z-2-(2-acetamidothiazol-4-yl)-3-(tetrahydrothiapyran-3-yl)₁propenoate.

The product from Example 6b (2.7g) in dry DMF (10 ml) was treated with N-acetylthiourea (1.3g) and the mixture heated at 95° for 4 hr. After cooling the mixture was diluted with ethyl acetate and the organic solution washed thoroughly with water. The solution was dried over anhydrous magnesium sulphate and evaporated to give a brown oil. Chromatography of the residue on silica gel using ethyl acetate-hexane (2:3) as eluant gave the title product as a colourless solid (1.01g). $\nu_{max}$(CHCl$_3$) 3450, 3000, 1700, 1540; δ(CDCl$_3$, 250 MHz) 2.85–3.1 (1H, m, tetrahydrothiapyranyl CH), 3.89 (3H, s, CO$_2$CH$_3$), 6.63 (1H, d, J=10Hz, acrylic -H), 6.97 (1H, s, thiazole -H), 8.96 (1H, brs, CH$_3$CONH) m/e 326 (M+).

(d) Z-[2-(2-aminothiazol-4-yl)-3-(tetrahydrothiapyran-3-yl)₁propenoic acid.

Methyl Z-[2-(2-acetamidothiazol-4-yl)-3-(tetrahydrothiapyran-3-yl)]propenoate (420 mg) was hydrolysed as in Example 1d. Work-up gave the title acid as a pale brown foam (270 mg). $\nu_{max}$(KBr) 1700, 1620, 1560 and 1530 cm$^{-1}$. δ[(CD$_3$)$_2$SO, 250 MHz]inter alia 6.34 (1H, d, J=10Hz), 6.43 (1H, s), 7.06 (2H, s).

(e) Sodium 6β-[Z-2-(2-aminothiazol-4-yl)-3-tetrahydrothiapyran-3-yl)₁propenamido penicillanate Z-[2-(2-aminothiazol-4-yl)-3-(tetrahydrothiapyran-3-yl)]propenoic acid (230 mg) was coupled to 6-aminopenicillanic acid (180 mg) using the mesyl chloride procedure described in Example 2f. Chromatography of the worked-up product o HP20SS eluting with acetone water mixtures, followed by concentration of the appropriate fractions to a low volume and freeze drying gave the title penicillin (180 mg) $\nu_{max}$(KBr) 1765, 1660(sh), 1610 and 1530 cm$^{-1}$. δ[(CH$_3$)$_3$SO, 250 MHz]inter alia 1.46 and 1.52 (6H, 2s, 2×CH$_3$), 3.84 (1H, s, 3-H), 5.3–5.5 (2H, m, 5-H and 6-H), 6.10, 6.12 (1H, 2d, acrylic-H), 6.24, 6.25 (1H, 2s, 5¹-H), 7.05 (2H, s, NH$_2$), 9.00, 9.03 (1H, 2d, CONH).

(f) 1-Acetoxyethyl 6β-[Z-2(2-aminothiazol-4-yl)-3-(tetrahydrothiapyran-3-yl)₁propenamido penicillanate Sodium 6β-[Z-2-(2-aminothiazol-4-yl)-3-(tetrahydropyran-3-yl)]propenamido penicillanate (250 mg) in N-methylpyrrolidinone (6 ml) was cooled to 0° and potassium carbonate (112 mg) added. 1-Bromoethylacetate (0.134g) was then added and the mixture stirred at 0° for 1 hr. The mixture was diluted with ethyl acetate and the organic solution washed with water, brine and then dried over anhydrous magnesium sulphate. Evaporation of the solvent and chromatography of the residue on silica gel using ethyl acetate as eluant gave the title ester as a buff foam (150 mg) $\nu_{max}$(CHCl$_3$) 3400, 3000, 1790(sh), 1770, 1675, and 1605 cm$^{-1}$; δ(CDCl$_3$, 250 MHz) inter alia 2.05, 2.08, 2.09, 2.11 (3H, 4s, —OCH(CH$_3$)o), 4.41, 4.42, 4.46, 4.47 (1H, 4s, 3-H), 5.5–5.85 (2H, m, 5-H and 6-H), 6.4–6.6 (2H, m, 5¹-H and acrylic-H).

EXAMPLE 7

Sodium 6β-[Z-2-(2-aminothiazolyl)-3-(tetrahydrothiapyran-2-yl)₁-propenamido penicillanate (a) 2-(2-Tetrahydrothiapyranylidene)-3-oxo-4-chlorobutyric acid, methyl ester.

Methyl-4-chloroacetoacetate (0.45g) in dry methlene dichloride (5 ml) containing 4A molecular sieve (3g) was treated with tetrahydrothiapyran-2-carboxylate (0.4g) and then piperidine (2 drops) and acetic acid (2 drops). The mixture was stirred at room temperature for 45 min. The solution was diluted with methylene dichloride and the organic solution washed with water and brine. After drying over anhydrous magnesium sulphate the solvent was evaporated. Chromatography of the residue on silica gel using ethyl acetate-hexane (1:5) as eluant gave the title product as a 2:1 (Z/E) mixture of isomers (0.43g). $\nu_{max}$(CHCl$_3$) 1710 and 1625 cm$^{-1}$.

(b) Methyl-Z-2-(2-acetamidothiazol-4-yl)-3-tetrahydrothiapyran-2-yl)₁propenoate

The product from Example 7a (0.43g) in dry DMF (7 ml) was treated with N-acetylthiourea (0.19g) and the mixture heated at 90° for 30 min. Solution was cooled, diluted with excess ethyl acetate and the resulting solution washed thoroughly with water. After drying over anhydrous magnesium sulphate the solvent was evaporated. Chromatography of the residue on silica gel using ethyl acetate-hexane (1:3) as eluant gave the title product as an orange solid (112 mg) δ(CDCl₃, 250 MHz) inter alia. 2.23 (3H, s, CH₃CONH), 3.89 (3H, s, CO₂CH₃), 6.64 (1H, d, $J=\overline{10}$Hz, acrylic —CH), 7.00 (1H, s, thiazole 5-H).

(c) Z-(2-aminothiazol-4-yl)-3-(tetrahydrothiapyran2-yl)₁propenoic acid.

Methyl [Z-(2-acetamidothiazol-4-yl)-3-(tetrahydrothiapyran-2-yl)]propenoate (112 mg) was hydrolysed as in Example 1d to give the title acid as a buff solid (44 mg).

(d) Sodium 6β-[Z-2-(2-aminothiazol-4-yl)₁-3-(tetrahydrothiapyran-2-yl)propenamido penicillanate The product from Example 7c (44 mg) was coupled to 6-aminopenicillanic acid (44 mg) using the active ester procedure described in Example le. After a conventional work-up procedure the crude sodium salt was applied to an HP20SS column. Chromatography, eluting with acetone-water mixture, gave the title compound (35 mg) after freeze drying the appropriate fractions. $v_{max}$(KBr) 1770, 1660, 1620, and 1520 cm⁻¹; δ[(CD₃)₂SO, 400 MHz]inter alia 1.49, 1.54 (6H, 2, s, 2×CH₃), 3.89, 3.90 (1H, 2s, 3-CH), 5.42-5.5 (2H, m, 5 and 6-H), 6.14, 6.16 (1H, 2d, acrylic -H), 6.37, 6.38 (1H, 2s, thiazole 5-H), 8.64, 8.74 (1H, 2d, $\overline{CONH}$).

We claim:
1. A compound of formula (I)

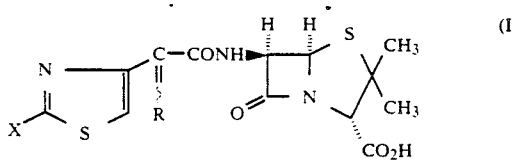

or a pharmaceutically acceptable salt or in vivo hydrolyzable ester thereof wherein X is hydrogen or a group NHR¹, wherein R¹ is hydrogen or an amino protecting group, R is a 5-membered or 6-membered saturated heterocyclic group containing 1 or 2 heteroatoms selected from the group consisting of oxygen, sulphur and nitrogen, unsubstituted or substituted by at least one moiety selected from the group consisting of alkyl of 1 to 6 carbon atoms, alkanoyl of 1 to 6 carbon atoms, alkoxy of 1 to 6 carbon atoms, halogen and cycloalkyl of 3 to 7 carbon atoms.

2. A compound according to claim 1 wherein R is tetrahydropyranyl.

3. A compound according to claim 1 which ii the syn-isomer of formula (IA):

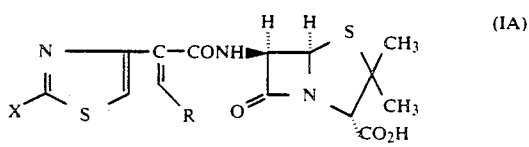

wherein X is hydrogen or a group NYHR¹, wherein R¹ is hydrogen or an amino protecting group, R is a 5-membered or 6-membered saturated heterocyclic group containing 1 or 2 heteroatoms selected from the group consisting of oxygen, sulphur and nitrogen, unsubstituted or substituted by at least one moiety selected from the group consisting of alkyl of 1 to 6 carbon atoms, alkanoyl of b 1 to 6 carbon atoms, alkoxy of 1 to 6 carbon atoms, halogen and cycloalkyl of 3 to 7 carbon atoms.

4. A compound according to claim 1 which is selected from the group consisting of:
2β-[Z-[2-(2-aminothiazol-4-yl)-3-(tetrahydro-4H-pyran-4-yl)]propenamido]penicillanic acid,
6β-[Z-2-(2-aminothiazol-4-yl)-3l-(tetrahydrothiapyran-4l-yl)]propenamidopenicillanic acid,
6β-[Z-2l-(2-aminothiazol-4-yl)-3-(tetrahydropyran-3-yl)]propenamido penicillanic acid,
6β-[Z-2-(2l-aminothiazol-4-yl)-3l-(tetrahydropyran-2-yl)]propenamido penicillanic acid,
6β-[Z-2-(2l-aminothiazol-4-yl)-3-(tetrahydrothiophen-3-yl)]propenamido penicillanic acid,
6β-[Z-2-(2l-aminothiazol-4-yl)-3-(tetrahydrothiapyran-3-yl)]propenamido penicillanic acid, and
6β-[Z-2-(2l-aminothiazol-4-yl)-3-(tetrahydrothiapyran-2-yl)]propenamido penicillanic acid.

5. A compound of formula (III):

wherein Y is:

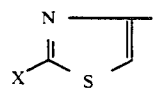

or a group which is convertible thereto, and wherein X is hydrogen or a group NHR¹, wherein R¹ is hydrogen or an amino protecting group, R is a 5-membered or 6-membered saturated heterocyclic group containing 1 or 2 heteroatoms selected from the group consisting of oxygen, sulphur and nitrogen, unsubstituted or substituted with at least one moiety selected from the group consisting of alkyl of 1 to 6 carbon atoms, alkanoyl of 1 to 6 carbon atoms, alkoxy of 1 to 6 carbon atoms, halogen and cycloalkyl of 3 to 7 carbon atoms, or a salt, ester, or acylating derivative thereof.

6. An antibacterial pharmaceutical composition for the treatment of bacterial infections in humans and animals which comprises an antibacterially effective amount of a compound of formula (I):

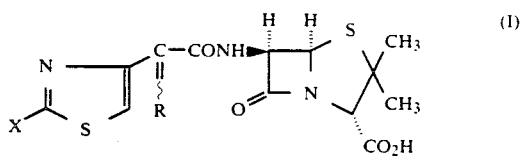

or a pharmaceutically acceptable salt or in vivo hydrolyzable ester thereof wherein X is hydrogen or a group NHR¹, wherein R¹ is hydrogen or an amino protecting group, R is a 5l-membered or 6-membered saturated heterocyclic group containing 1 or 2 heteroatoms selected from the group consisting of oxygen, sulphur and nitrogen, unsubstituted or substituted by at least one moiety selected from the group consisting of alkyl of 1 to 6 carbon atoms, alkanoyl of 1 to 6 carbon atoms, alkoxy of 1 to 6 carbon atoms, halogen and cycloalkyl of 3 to 7 carbon atoms, in combination with a pharmaceutically acceptable carrier.

7. A composition according to claim 6 wherein R is tetrahydropyranyl.

8. A composition according to claim 6 wherein the compound is the syn-isomer of formula (IA):

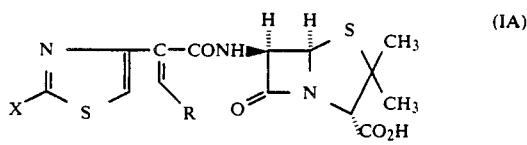

wherein X is hydrogen or a group $NHR^1$, wherein $R^1$ is hydrogen or an amino protecting group, R is a 5-membered or 6-membered saturated heterocyclic group containing 1 or 2 heteroatoms selected from the group consisting of oxygen, sulphur and nitrogen, unsubstituted or substituted by at least one moiety selected from the group consisting of alkyl of 1 to 6 carbon atoms, alkanoyl of 1 to 6 carbon atoms, alkoxy of 1 to 6 carbon atoms, halogen and cycloalkyl of 3 to 7 carbon atoms.

9. A composition according to claim 6 wherein the compound is selected from the group consisting of:
2β-[Z-[2-(2-aminothiazol-4-yl)-3-(tetrahydro-4H-pyran-4-yl)]propenamido]penicillanic acid,
6β-[Z-2-(2l-aminothiazol-4-yl)-3-(tetrahydrothiapyran-4-yl)]propeneamidopenicillanic acid,
6β-[Z-2l-(2-aminothiazol-4-yl)-3-(tetrahydropyran-3l-yl)]propenamido penicillanic acid,
6β-[Z-2-(2l-aminothiazol-4-yl)-3-(tetrahydropyran-2-yl)]propenamido penicillanic acid,
6β-[Z-2-(2-aminothiazol-4-yl)-3-(tetrahydrothiophen-3-yl)]propenamido penicillanic acid,
6β-[Z-2l-(2-aminothiazol-4-yl)-3-(tetrahydrothiapyran-3-yl)]propenamido penicillanic acid and
6β-[Z-2-(2-aminothiazol-4-yl)-3-(tetrahydrothiapyran-2-yl)]propenamido penicillanic acid.

10. A method of treating bacterial infections in humans or animals, which method comprises administering to a patient in need thereof an antibacterially effective amount of a compound of formula (I):

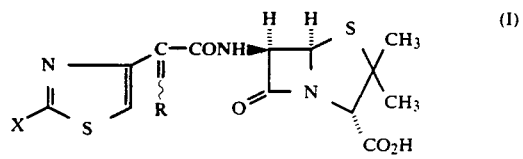

or a pharmaceutically acceptable salt or in vivo hydrolyzable ester thereof wherein X is hydrogen or a group $NHR^1$, wherein $R^1$ is hydrogen or an amino protecting group, R is a 5-membered or 6-membered saturated heterocyclic group containing 1 or 2 heteroatoms selected from the group consisting of oxygen, sulphur and nitrogen, unsubstituted or substituted by at least one moiety selected from the group consisting of alkyl of 1 to 6 carbon atoms, alkanoyl of 1 to 6 carbon atoms, alkoxy of 1 to 6 carbon atoms, halogen and cycloalkyl of 3 to 7 carbon atoms, in combination with a pharmaceutically acceptable carrier.

11. A method according to claim 10 wherein R is tetrahydropyranyl.

12. A method according to claim 10 wherein the compound is the syn-isomer of formula (IA):

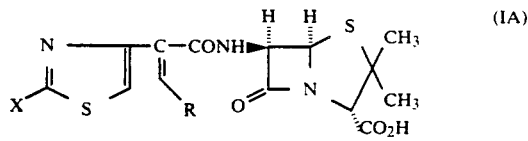

wherein X is hydrogen or a group $NHR^1$, wherein $R^1$ is hydrogen or an amino protecting group, R is a 5-membered or 6-membered saturated heterocyclic group containing 1 or 2 heteroatoms selected from the group consisting of oxygen, sulphur and nitrogen, unsubstituted or substituted by at least one moiety selected from the group consisting of ally of 1 to 6 carbon atoms, alkanoyl of 1 to 6 carbon atoms, alkoxy of 1 to 6 carbon atoms, halogen and cycloalkyl of 3 to 7 carbon atoms.

13. A method according to claim 10 wherein the compound is selected from the group consisting of:
2β-[Z-2-(2-aminothiazol-4-yl)-3l-(tetrahydro-4H-pyran-4-yl)]propenamido]penicillanic acid,
6β-[Z-2-(2l-aminothiazol-4yl)-3-(tetrahydrothiapyran-4-yl)]propeneamidopenicillanic acid,
6β-[Z-2-(2-aminothiazol-4l-yl)-3-(tetrahydropyran-3l-yl)]propenamido penicillanic acid,
6β-[Z-2-(2-aminothiazol-4-yl)-3-(tetrahydropyran-2-yl)]propenamido penicillanic acid;
6β-[Z-2-(2l-aminothiazol-4-yl)-3-(tetrahydrothiophen-3-yl)]propenamido penicillanic acid,
6β-[Z-2l-(2l-aminothiazol-4-yl)-3-(tetrahydrothiapyran-3-yl)]propenamido penicillanic acid and
6β-[Z-2l-(2l-aminothiazol-4-yl)-3-(tetrahydrothiapyran-2-yl)]propenamido penicillanic acid.

* * * * *